(12) United States Patent
Kim

(10) Patent No.: US 12,156,740 B2
(45) Date of Patent: Dec. 3, 2024

(54) TRANSPARENT ORTHODONTIC APPLIANCE REMOTE MONITORING SYSTEM

(71) Applicant: GNI CO., LTD., Hwaseong-si (KR)

(72) Inventor: Dug Soo Kim, Hwaseong-si (KR)

( * ) Notice: Subject to any disclaimer, the term of this patent is extended or adjusted under 35 U.S.C. 154(b) by 352 days.

(21) Appl. No.: 17/640,170

(22) PCT Filed: Aug. 18, 2021

(86) PCT No.: PCT/KR2021/010971
§ 371 (c)(1),
(2) Date: Mar. 3, 2022

(87) PCT Pub. No.: WO2022/158673
PCT Pub. Date: Jul. 28, 2022

(65) Prior Publication Data
US 2023/0157633 A1     May 25, 2023

(30) Foreign Application Priority Data
Jan. 20, 2021  (KR) ......................... 10-2021-0007795

(51) Int. Cl.
  *A61B 5/00*   (2006.01)
  *A61C 7/00*   (2006.01)
  *A61C 7/08*   (2006.01)

(52) U.S. Cl.
CPC ............ *A61B 5/4833* (2013.01); *A61C 7/002* (2013.01); *A61C 7/08* (2013.01)

(58) Field of Classification Search
CPC ........... A61B 5/4833; A61B 5/48; A61B 5/44; A61C 7/002; A61C 7/08; A61C 7/00; A61C 19/04
(Continued)

(56) References Cited

U.S. PATENT DOCUMENTS

| 2018/0000565 | A1 | 1/2018 | Shanjani et al. |
| 2020/0046461 | A1 | 2/2020 | Shanjani et al. |
| 2021/0038153 | A1* | 2/2021 | Claflin ................. A61B 5/0004 |

FOREIGN PATENT DOCUMENTS

| KR | 10-2006-0085158 A | 7/2006 |
| KR | 10-2017-0004401 A | 1/2017 |

(Continued)

*Primary Examiner* — Ralph A Lewis
*Assistant Examiner* — Mirayda A Aponte
(74) *Attorney, Agent, or Firm* — KORUS Patent, LLC; Seong Il Jeong

(57) ABSTRACT

Provided is a transparent orthodontic appliance remote monitoring system that includes a clear aligner worn on teeth for orthodontic treatment; a contact sensor module installed inside the clear aligner to detect wearing of the clear aligner on teeth through contact therewith; a user terminal that receives a signal from the contact sensor module and calculates a wearing time of the clear aligner from the received signal using an application; and a server computer for sharing information calculated in the user terminal to a clinic in charge, wherein the clear aligner has a tooth insertion groove into which the teeth are inserted, wherein a mounting groove for mounting the contact sensor module is formed on an inner surface of the tooth insertion groove, wherein the mounting groove is formed to correspond to a tooth of the teeth with the least displacement between before and after the orthodontic treatment.

2 Claims, 6 Drawing Sheets

(58) Field of Classification Search
USPC .............................................................. 433/6
See application file for complete search history.

(56) References Cited

FOREIGN PATENT DOCUMENTS

| | | |
|---|---|---|
| KR | 10-2017-0017975 A | 2/2017 |
| KR | 10-2017-0026304 A | 3/2017 |
| KR | 10-2019-0027209 A | 3/2019 |
| KR | 10-2019-0067129 A | 6/2019 |
| KR | 10-2019-0101231 A | 8/2019 |
| WO | 2019/108978 A1 | 6/2019 |

* cited by examiner

TRANSPARENT ORTHODONTIC APPLIANCE REMOTE MONITORING SYSTEM

FIELD OF THE INVENTION

The present invention relates to a transparent orthodontic appliance remote monitoring system, and more particularly, to a transparent orthodontic appliance remote monitoring system using a clear aligner and a sensor installed on the clear aligner.

BACKGROUND OF THE INVENTION

Various orthodontic methods are used to correct malocclusion. Malocclusion refers to an occlusion with an esthetic or functional problem when the teeth are not aligned or the occlusion between the upper and lower teeth is out of the normal range. In the case of malocclusion, in addition to aesthetic and functional problems, food debris is likely to remain between the teeth because the teeth are not evenly aligned, and thus, it is difficult to keep the teeth clean even with brushing. Accordingly, various dental or gum diseases may be caused due to malocclusion. Orthodontic treatment is to treat such malocclusion. Orthodontic treatment uses the movable property of teeth when subjected to continuous external force. Among the appliance for orthodontic treatment, the most used in these days includes brackets attached to the teeth and a wire connecting the brackets. This appliance corrects malocclusion by continuously moving the teeth using the pulling force of the wire connecting the brackets. However, since the bracket and the wire in this appliance are mounted on the teeth throughout a long treatment time, patients experience discomfort. In addition, since the bracket and the wire are visible to others, it is also a disadvantage in view of aesthetic.

In order to solve such drawbacks, an orthodontic method using a clear aligner has been proposed. The transparent orthodontic method using the clear aligner corrects the teeth by sequentially using the clear aligners corresponding to the teeth's arrangements that change in stages from the state of the teeth before orthodontic treatment to the state after orthodontic treatment. Since the clear aligner can be easily removed by the patient, there is relatively less discomfort compared to other devices, and since the clear aligner is made of transparent plastic, it has an advantage of having an excellent aesthetic property.

However, the method of orthodontic treatment using the removable clear aligner is often ineffective because in many cases, patients do not follow a doctor's instruction for the wearing time of the clear aligner. For example, if a doctor has instructed that the clear aligner be worn for 8 hours or more per day, the patient wears the clear aligner only for a shorter period, and thus, the orthodontic effect is reduced.

DETAILED DESCRIPTION OF THE INVENTION

Technical Problems

The object of the present invention is to provide a system and a method capable of solving the problem of poor or delayed orthodontic results caused by the patient's non-compliance with a doctor's instruction for the wearing time of the clear aligner.

Summary of the Invention

A transparent orthodontic appliance remote monitoring system according to one perspective of the present invention, comprises: a clear aligner 100 worn on teeth for orthodontic treatment; a contact sensor module 200 installed inside the clear aligner 100 to detect wearing of the clear aligner 100 on teeth through contact therewith; a user terminal 300 that receives a signal from the contact sensor module 200 and calculates a wearing time of the clear aligner 100 from the received signal using an application, and a server computer 400 for sharing information calculated in the user terminal 300 to a clinic in charge, wherein the clear aligner 100 has a tooth insertion groove 120 into which the teeth are inserted, wherein a mounting groove 140 for mounting the contact sensor module 200 is formed on an inner surface of the tooth insertion groove 120, wherein the mounting groove 140 is formed to correspond to a tooth of the teeth with the least displacement during the orthodontic treatment.

According to one embodiment, the contact sensor module 200 includes a sensor 220 detecting a mechanical stimulus and a flexible encapsulation unit 240 molded to encapsulate the sensor 220 with material having greater elasticity than that of the clear aligner 100, wherein the encapsulation unit 240 is pressed against the teeth to deform the sensor 220, and the sensor 220 detects wearing of the clear aligner 100 by the deformation.

According to one embodiment, a method of applying the transparent orthodontic appliance remote monitoring system comprises: counting the wearing time of the clear aligner 100 when the contact sensor module 200 detects wearing of the clear aligner 100; calculating a time for which the clear aligner 100 is worn once when the clear aligner 100 is separated from the mouth; calculating a daily wearing time of the clear aligner 100 when a day has elapsed from a prestored setting time, and comparing the calculated actual daily wearing time of the clear aligner 100 with a predetermined standard wearing time, and if the actual daily wearing time is less than the standard wearing time, generating an alarm and counting a wearing time of the clear aligner 100 for the next day.

Technical Effects of the Invention

According to the present invention, it is possible to solve the problem of poor or delayed orthodontic results caused by the patient's non-compliance with a doctor's instruction for the wearing time of the clear aligner.

BEST MODE FOR THE INVENTION

Hereinafter, embodiments of the present invention will be described in detail with reference to the accompanying drawings, so that one of ordinary skill in the art to which the present invention pertains can easily implement them. The present invention may be embodied in several different forms and is not limited to the embodiments described herein.

In order to clearly explain the present invention, components or elements irrelevant to the present invention are omitted, and the same reference numbers are used to denote the same or similar components or elements throughout the specification.

In addition, in various embodiments, the same components or elements are denoted by using the same reference numbers and described only in the representative embodiment, and in other embodiments, only certain configurations that is different from those in the representative embodiment will be described.

Throughout the specification, when a part, component, or element is described to be "connected" to another part, component, or element, it includes not only configurations where they are "directly connected," but also where they are "indirectly connected" with another member interposed therebetween. In addition, when it is described that a part "includes" a certain component or element, this may mean that the part further includes other components or elements rather than excluding other components or elements unless otherwise stated.

Figure 1:
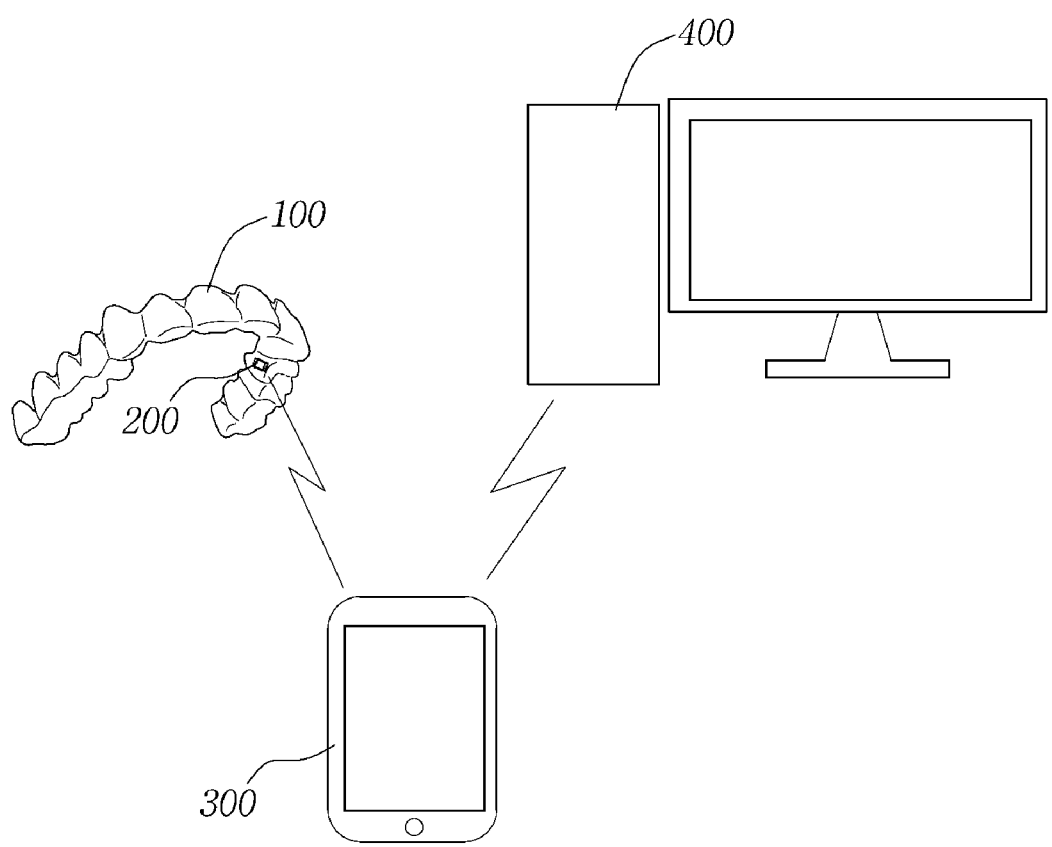
FIG. 1 is a diagram for explaining a transparent orthodontic appliance remote monitoring system according to an embodiment of the present invention.
Figure 2:
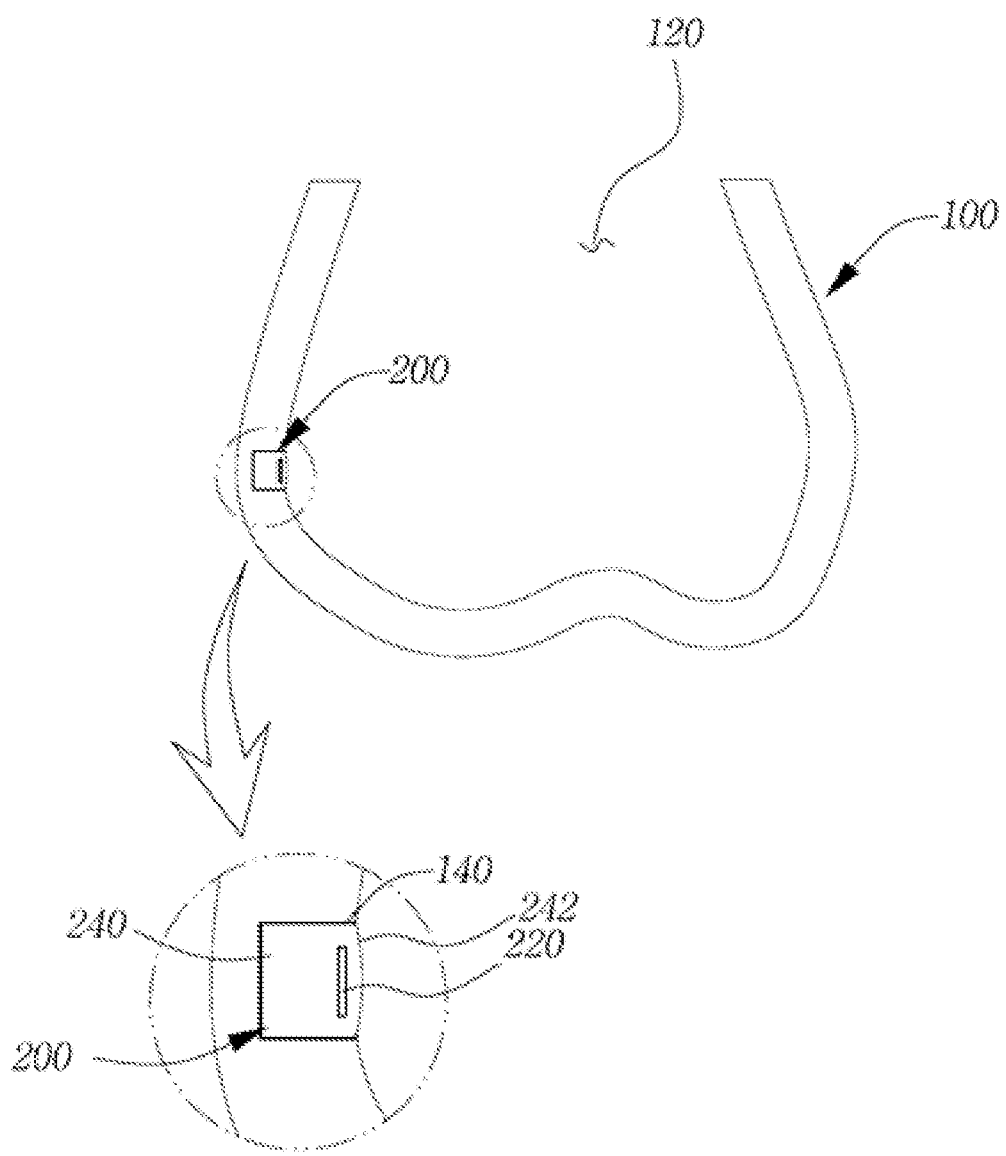
FIG. 2 is a cross-sectional view illustrating a clear aligner provided in the transparent orthodontic appliance remote monitoring system of FIG. 1 according to an embodiment of the present invention.

FIG. 1 is a diagram for explaining a transparent orthodontic appliance remote monitoring system according to an embodiment of the present invention. FIG. 2 is a cross-sectional view illustrating a clear aligner provided in the transparent orthodontic appliance remote monitoring system of FIG. 1 according to an embodiment of the present invention.

As shown in FIGS. 1 and 2, a transparent orthodontic appliance remote monitoring system according to an embodiment of the present invention comprises: a clear aligner 100 worn on teeth for orthodontic treatment; a contact sensor module 200 installed inside the clear aligner 100 to detect wearing of the clear aligner 100 on teeth through contact therewith; a user terminal 300 that receives a signal from the contact sensor module 200 and calculates a wearing time of the clear aligner 100 based on the received signal using an application, and a server computer 400 for sharing information calculated in the user terminal 300 to a clinic in charge.

The clear aligner 100 is formed by molding a transparent resin material to include a shape corresponding to each of the teeth. The clear aligner 100 has a tooth insertion groove 120 into which the patient's upper or lower teeth are inserted. In addition, a mounting groove 140 for mounting the contact sensor module 200 is formed on the inner surface of the tooth insertion groove 120 of the clear aligner 100. The mounting groove 140 is formed to correspond to the height of contour of a tooth that has no displacement or the least displacement between before and after orthodontic treatment based on orthodontic treatment plan. By installing the contact sensor module 200 to correspond to the tooth with little displacement between before and after orthodontic treatment, it is possible to solve the problem that the contact sensor module 200 cannot detect the teeth due to the displacement of the tooth being in contact with the contact sensor module 200.

The contact sensor module 200 includes a sensor 220 detecting a mechanical stimulus and a flexible encapsulation unit 240 molded to encapsulate the sensor 220. It is desired that the sensor 220 is a thin film sensor with minimal external change. In addition, the sensor 220 may include a wireless communication unit for wireless communication with the user terminal 300. The wireless communication unit may use, for example, a method of a short-range wireless communication or a near-field communication (NFC). In addition, the sensor 220 may include a wirelessly rechargeable battery. The encapsulation unit 240 may be formed of a material, such as silicone material, that is softer and has greater viscosity and elasticity compared to the material of the clear aligner 100. The encapsulation unit 240 has a front convex surface 242, and other portions other than the front convex surface 242 are completely accommodated in the mounting groove 140. When the patient's teeth are inserted into the tooth insertion groove 120 of the clear aligner 100, the front convex surface 242 is pressed and retracted backward. Accordingly, the front convex surface 242 is deformed, and thus, the sensor 220 is pressed backward. The sensor 220 detects this pressing force and provides a signal indicating that the clear aligner 100 is mounted on the patient's teeth, to the user terminal 300. As mentioned above, the mounting groove 140 is formed to correspond to the height of contour of the tooth that has no displacement or the least displacement between before and after orthodontic treatment based on orthodontic treatment plan. The contact sensor module 200 is inserted and installed in the mounting groove 140 and is pressed by the height of contour of the most stable tooth. More preferably, the mounting groove 140 is formed to correspond to the lingual side of the height of contour, and the contact sensor module 200 is arranged to contact the lingual side of the height of contour of the most stable tooth.

Figure 4:
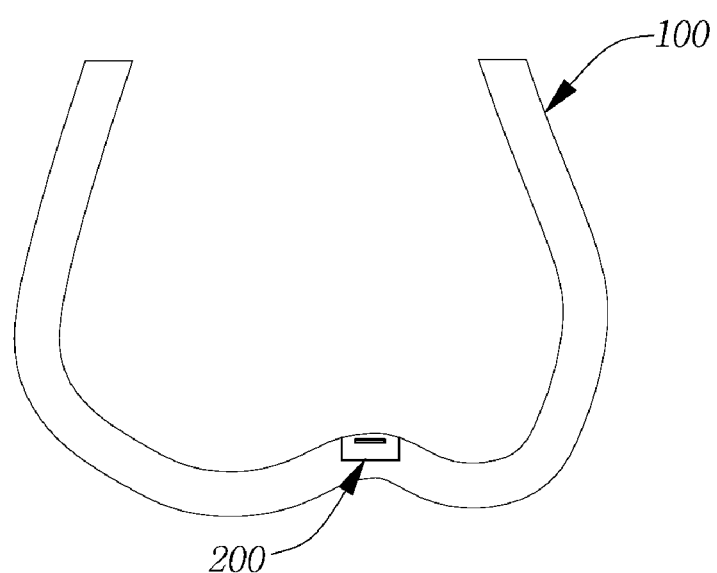
FIG. 4 is a drawing for explaining a position of a mounting groove and a contact sensor module, which is advantageous for a clear aligner and a power aligner to which a bracket and a wire are applied.

In this embodiment, the clear aligner 100 may be applied together with a lingual wire orthodontic appliance in which a bracket and an orthodontic wire are installed on the lingual side of the teeth. An orthodontic appliance including such wire orthodontic appliance and the clear aligner 100 is defined as a "Power Cligner." When the power cligner is applied, since the wire orthodontic appliance is applied to the lingual side, it is advantageous to form a mounting groove to correspond to the tip of the tooth and to install the contact sensor module 200 in the mounting groove as shown in FIG. 4.

It is desired that the user terminal 300 is a mobile communication terminal such as a smartphone or tablet PC. The user terminal 300 receives a signal from the contact sensor module 200 and calculates the patient's wearing time of the clear aligner 100. The calculation of the wearing time includes a daily wearing time and a cumulative wearing time from the patient's visit to the clinic to the next visit.

The patient's wearing time of the clear aligner 100 is calculated and stored through the application of the user terminal 300 and transmitted to the computer 400 of the clinic. The doctor in the clinic compares a minimum wearing time, which is a standard cumulative wearing time, of the clear aligner 100 instructed by the doctor with an actual cumulative wearing time that the patient wears the clear aligner 100. The doctor provides the information to the patient and utilizes the information for orthodontic treatment. In addition, the user terminal 300 compares an actual daily wearing time of the patient with a standard daily wearing time instructed by the doctor through the application, and when the actual daily wearing time is less than the standard daily wearing time, the user terminal 300 generates a visual or auditory alarm sound.

In addition, the user terminal 300 compares and shows the daily wearing time of the previous day and the standard daily wearing time instructed by the doctor on one screen through the display unit. In addition, the user terminal 300 compares the cumulative wearing time up to now with the standard cumulative wearing time through the display unit and displays it on one screen. The user terminal 300 share the wearing time information, which is processed, stored, and displayed in the user terminal 300, with the external computer 400 of the clinic. Accordingly, the external computer 400 displays the daily wearing time and the cumulative wearing time of the patient through a display unit. In this case, the standard daily wearing time and the standard cumulative wearing time instructed to the patient are also displayed.

The contact sensor module 200 and the user terminal 300 may exchange signals through wireless communication such as Bluetooth communication. Accordingly, sensor displacement information, information on whether the clear aligner 100 is worn, measured by the contact sensor module 200 is provided to the user terminal 300 in real time. The user terminal 300 calculates the daily wearing time and the cumulative wearing time of the clear aligner 100 based on the information provided by the contact sensor module 200, and stores and displays the calculated information. The information is transmitted to the computer 400 of the clinic in a remote location.

A method of applying the transparent orthodontic appliance remote monitoring system described above is as shown in FIG. 3.

Figure 3:
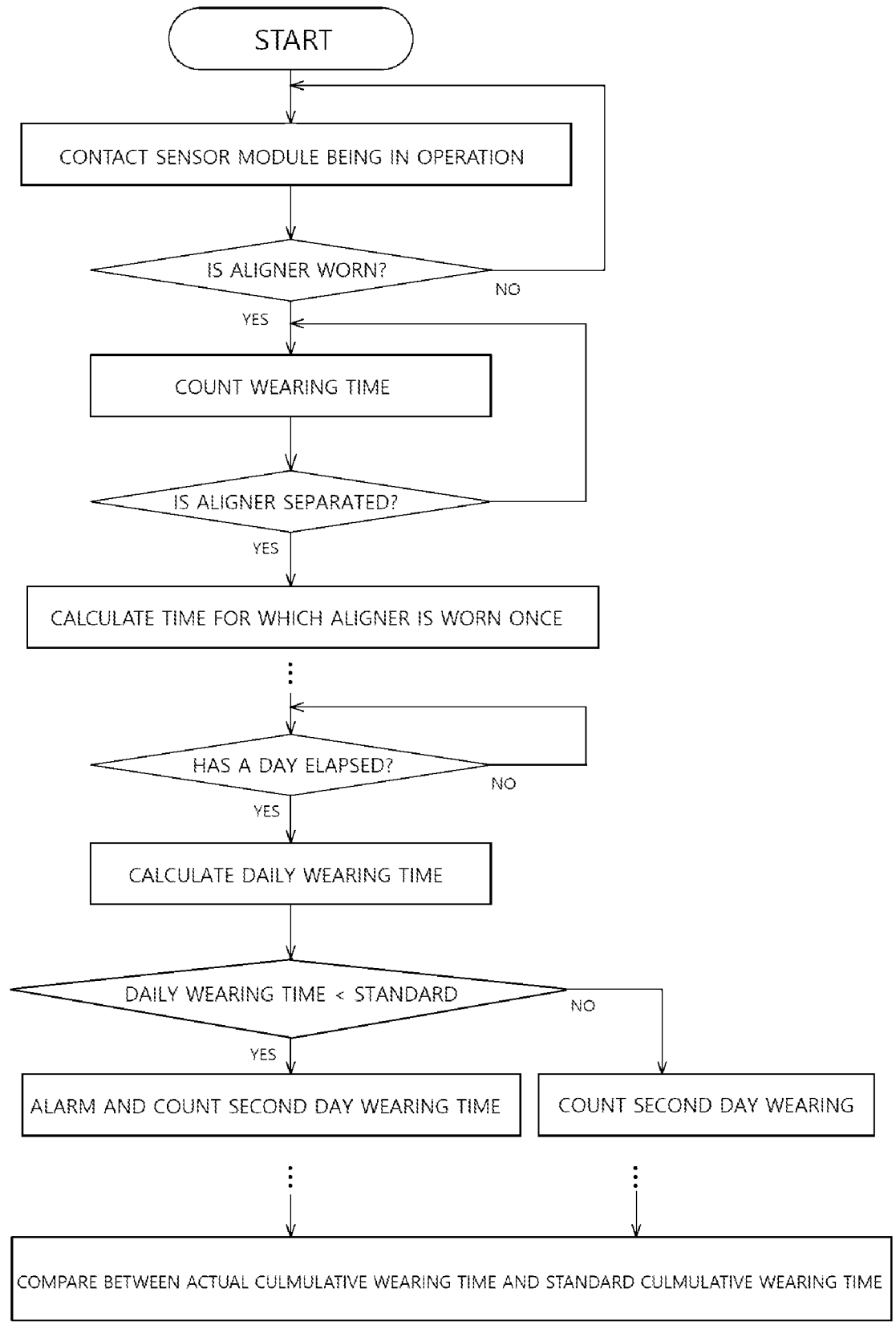
FIG. 3 is a drawing for explaining a method of applying the transparent orthodontic appliance remote monitoring system of FIGS. 1 and 2 according to an embodiment of the present invention.

Referring to FIGS. 1 and 3 together, while the contact sensor module 200 is in operation, when the clear aligner 100 is worn on the teeth, the contact sensor module 200 detects wearing of the clear aligner 100, and the user terminal 300, which can communicate with the contact sensor module 200 through wireless communication, counts the wearing time of the clear aligner 100. When the patient separates the clear aligner 100 from the mouth, the user terminal 300 receives a signal from the contact sensor module 200 to determine the separation and calculates a time for which the patient wears the clear aligner 100 once. In this way, each time the patient puts on and separates the clear aligner 100, the wearing time is calculated. In addition, the user terminal 300 determines whether a day has elapsed from a setting time prestored through the application. When a day has elapsed, the user terminal 300 calculates a daily wearing time of the clear aligner 100, which is a total cumulative wearing time for which the patient has worn the clear aligner 100 during the day. The calculated actual wearing time of the clear aligner 100 is compared with the standard wearing time. When the actual daily wearing time is less than the standard daily wearing time, an alarm is generated, and the wearing time for the second day is counted with the alarm. In this case, the display unit of the user terminal 300 displays the comparison between the actual daily wearing time and the standard daily wearing time. On the other hand, if the actual daily wearing time day is equal to or greater than the standard daily wearing time, the wearing time for the second day is counted without generating an alarm. Alarms may be provided by periodically generating sounds and/or vibrations. In addition, in the next visit to the clinic, the user terminal 300 compares the actual total cumulative wearing time with the standard cumulative wearing time, and the comparison result is displayed through the monitor of the computer 400 in the clinic.

Figure 5:
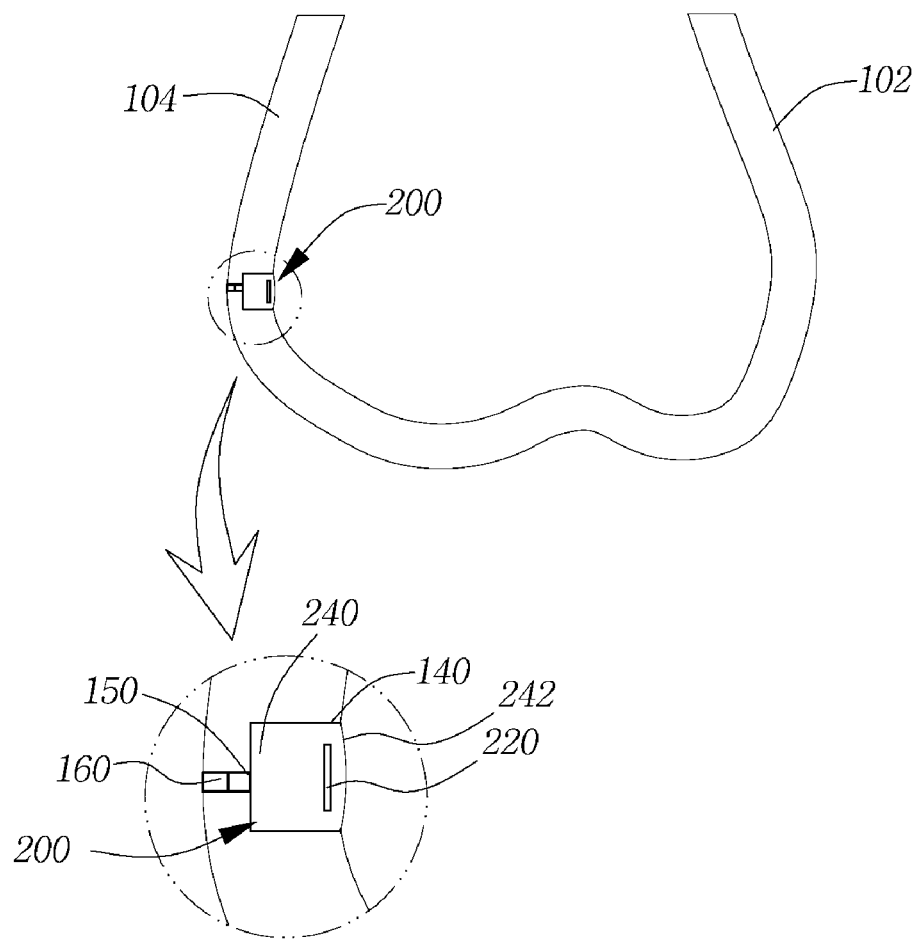
FIG. 5 is a drawing for explaining another example of a clear aligner and a contact sensor module.

FIG. 5 is a drawing for explaining another example of a clear aligner and a contact sensor module.

Referring to FIG. 5, a clear aligner 100 includes a first wall 102, or an anterior wall, and a second wall 104, or a posterior wall, facing each other to define a tooth insertion groove 120. A mounting groove 140 for mounting a sensor module is formed on the inner surface of the second wall 102.

The contact sensor module 200 includes a sensor 220 detecting a mechanical stimulus and a flexible encapsulation unit 240 molded to encapsulate the sensor 220. It is desired that the sensor 220 is a thin film sensor with minimal external change. In addition, the sensor 220 may include a wireless communication unit for wireless communication with the user terminal 300. The wireless communication unit may use, for example, a method of a short-range wireless communication or a near-field communication (NFC). In addition, the sensor 220 may include a wirelessly rechargeable battery. The encapsulation unit 240 may be formed of a material, such as silicone material, that is softer and has greater viscosity and elasticity compared to the material of the clear aligner 100. The encapsulation unit 240 has a front convex surface 242, and other portions other than the front convex surface 242 are completely accommodated in the mounting groove 140. When the patient's teeth are inserted into the tooth insertion groove 120 of the clear aligner 100, the front convex surface 242 is pressed and retracted backward. Accordingly, the front convex surface 242 is deformed, and thus, the sensor 220 is pressed backward. The sensor 220 detects this pressing force and provides a signal indicating that the clear aligner 100 is mounted on the patient's teeth, to the user terminal 300. As mentioned above, the mounting groove 140 is formed to correspond to the height of contour of the tooth that has no displacement or the least displacement between before and after orthodontic treatment based on orthodontic treatment plan. The contact sensor module 200 is inserted and installed in the mounting groove 140 and is pressed by the height of contour of the most stable tooth.

Meanwhile, a pinhole 150 is formed in the second wall 104 of the clear aligner 100 to be connected to the mounting groove 140 from the outside of the tooth insertion groove 120. The pinhole 150 is blocked by a blocking member 160 of soft resin material that is easily removed by inserting a pin. For replacement or wireless charging of the contact sensor module 200, it is necessary to separate the contact sensor module 200 from the clear aligner 100. In this case, by inserting a rigid pin capable of penetrating the blocking member 160 into the pinhole 150, the blocking member 160 is penetrated and the pin is further advanced to push the contact sensor module 200 out of the mounting groove 140.

Figure 6:
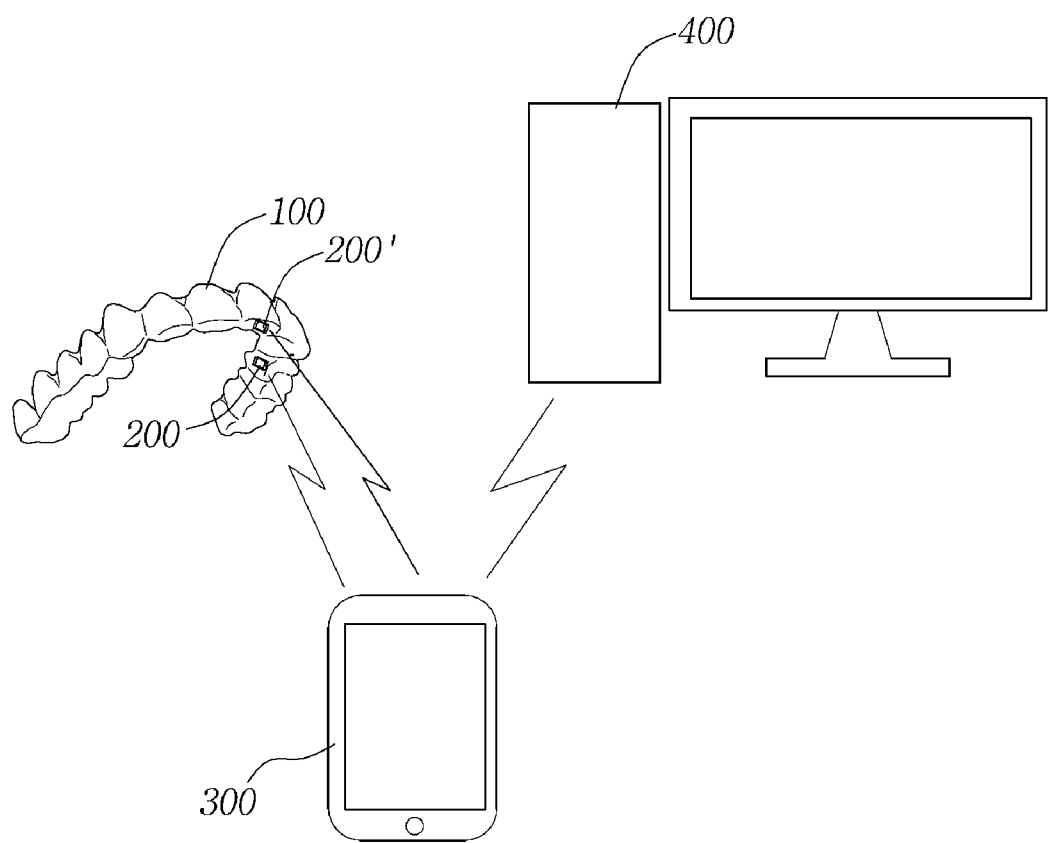
FIG. 6 is a diagram for explaining a transparent orthodontic appliance remote monitoring system according to another embodiment of the present invention.

FIG. 6 is a diagram for explaining a transparent orthodontic appliance remote monitoring system according to another embodiment of the present invention.

As shown in FIG. 6, a transparent orthodontic appliance remote monitoring system according to an embodiment of the present invention comprises: a clear aligner 100 worn on teeth for orthodontic treatment; a contact sensor module 200 installed inside the clear aligner 100 to detect wearing of the clear aligner 100 on teeth through contact therewith; a displacement measuring sensor module 200' detecting displacement of a specific tooth among the teeth on which the clear aligner 100 is mounted; a user terminal 300 that receives a signal from the contact sensor module 200 and a signal from the displacement measuring sensor module 200' and calculates a wearing time of the clear aligner 100 and displacement of the specific tooth based on the received signals using an application, and a server computer 400 for sharing information calculated in the user terminal 300 to a clinic in charge.

As described in the previous embodiment, the clear aligner 100 is formed to include a shape corresponding to the upper or lower teeth to be corrected. The clear aligner 100 is molded with a transparent resin material to include a shape corresponding to each of the teeth therein. The clear aligner 100 includes a tooth insertion groove into which the patient's upper or lower teeth are inserted. A first mounting groove and a second mounting groove are formed on the inner surface of the clear aligner 100. The contact sensor module 200 is inserted and mounted in the first mounting groove, and the displacement measuring sensor module 200' is inserted and mounted in the second mounting groove. The displacement measuring sensor module 200' is installed at a position corresponding to a tooth that has the largest displacement between before and after orthodontic treatment. The user terminal 300 can calculate a tooth displacement amount per wearing time of the clear aligner 100 through the application.

The present invention is not limited by the embodiments described above and can be embodied as various modifications.

What is claimed is:

1. A transparent orthodontic appliance remote monitoring system comprising:
    a clear aligner configured to be worn on teeth for orthodontic treatment;
    a contact sensor module installed inside the clear aligner to detect wearing of the clear aligner on the teeth through contact therewith;
    a user terminal that receives a signal from the contact sensor module and calculates a wearing time of the clear aligner from the received signal using a software program, and
    a server computer for sharing information calculated in the user terminal to a clinic in charge,
    wherein the clear aligner has a tooth insertion groove into which the teeth are inserted,
    wherein a mounting groove for mounting the contact sensor module is formed on an inner surface of the tooth insertion groove,
    wherein the mounting groove is configured to be located in the clear aligner corresponding to a tooth of the teeth with the least displacement during the orthodontic treatment,
    wherein the contact sensor module includes a sensor detecting a mechanical stimulus and a flexible encapsulation unit molded to encapsulate the sensor with material having greater elasticity than that of the clear aligner, wherein the encapsulation unit is pressed against the teeth to deform the sensor, and the sensor detects wearing of the clear aligner by the deformation,
    wherein the encapsulation unit comprises a front convex surface configured to face the teeth when the clear aligner is mounted on the teeth, and other portions other than the front convex surface, the other portions being configured to be completely accommodated in the mounting groove; and the sensor is configured to detect pressing force when the front convex surface is pressed by the teeth and provide the signal indicating that the clear aligner is mounted on the teeth, to the user terminal,
    wherein a pinhole is formed in a wall of the clear aligner to be connected to the mounting groove from an outside of the tooth insertion groove wherein a diameter of the pinhole is smaller than a width of the mounting groove and the pinhole is blocked by a blocking member of soft resin material that is configured to be removed or penetrated by inserting a pin.

2. A method of applying the transparent orthodontic appliance remote monitoring system of claim 1, the method comprises:
    counting the wearing time of the clear aligner when the contact sensor module detects wearing of the clear aligner;
    calculating a time for which the clear aligner is worn once when the clear aligner is separated from the mouth;
    calculating a daily wearing time of the clear aligner when a day has elapsed from a prestored setting time, and
    comparing the calculated actual daily wearing time of the clear aligner with a predetermined standard wearing time, and if the actual daily wearing time is less than the standard wearing time, generating an alarm and counting a wearing time of the clear aligner for the next day.

* * * * *